(12) United States Patent
Kato et al.

(10) Patent No.: US 6,992,178 B2
(45) Date of Patent: Jan. 31, 2006

(54) AGENT IMPARTING RESISTANCE TO EXTERNAL STIMULI

(75) Inventors: Yukio Kato, 6-9-501, Ushitawaseda 3-chome, Higashi-ku, Hiroshima-shi, Hiroshima 732-0062 (JP); Shinichi Tsutsumi, Maebashi (JP); Ryo Oda, Hiroshima (JP); Hideaki Shintani, Hiroshima (JP); Masahiro Nishimura, Hiroshima (JP)

(73) Assignees: Two Cells Co., Ltd., Hiroshima (JP); Yukio Kato, Hiroshima (JP); Koichiro Tsuji, Hiroshima (JP)

(*) Notice: Subject to any disclaimer, the term of this patent is extended or adjusted under 35 U.S.C. 154(b) by 0 days.

(21) Appl. No.: 10/416,178

(22) PCT Filed: Oct. 17, 2001

(86) PCT No.: PCT/JP01/09118

§ 371 (c)(1),
(2), (4) Date: Jan. 21, 2004

(87) PCT Pub. No.: WO02/40644

PCT Pub. Date: May 23, 2002

(65) Prior Publication Data

US 2004/0121301 A1 Jun. 24, 2004

(30) Foreign Application Priority Data

Nov. 15, 2000 (JP) .................................. 2000-348469

(51) Int. Cl.
*C07K 14/00* (2006.01)
*A61K 38/16* (2006.01)

(52) U.S. Cl. ................ 530/396; 514/8; 435/325
(58) Field of Classification Search ............... 514/8; 530/396

See application file for complete search history.

(56) References Cited

PUBLICATIONS

Gang, E. et al. Stem Cells 22: 617–624 (2004).*
Nishimura et al. Expermental Cell Research 295: 119–127 (2004).*
Yan et al. Journal of Biological Chemistry vol. 265, No. 17 10125–10131 (1990).*
Cavada et al. Current Protein and Peptide Science vol. 2, No. 2 125–135 (2001).*
WO 99/15628.*
Kollet, O. et al. Experimental Hematology 28: 726–736 (2000).*

* cited by examiner

*Primary Examiner*—Jon Weber
*Assistant Examiner*—Anand Desai
(74) *Attorney, Agent, or Firm*—Finnegan, Henderson Farabow, Garrett & Dunner, L.L.P.

(57) ABSTRACT

The invention provides an agent for conferring resistance comprising a lectin as an effective component, which are able to confer resistance against external stimuli to animal cells, particularly mammalian cells, and to their cultured cells and various tissues in the living bodies. The agent for conferring resistance to external stimulus according to the invention can confer to such animal cells and/or tissues resistance against mechanical stimuli and/or proteolytic reactions, and thereby enhance graft fixation of the cells and/or tissues, as well as transplant tissues obtained by culturing them.

14 Claims, 11 Drawing Sheets

AGENT IMPARTING RESISTANCE TO EXTERNAL STIMULI

CROSS REFERENCE TO RELATED APPLICATIONS

This application is a national phase application based on PCT/JP01/09118, filed Oct. 17, 2001, the content of which is incorporated herein by reference, and claims the priority of Japanese Patent Application no. 2000-348469, filed Nov. 15, 2000, the content of which is incorporated herein by reference.

TECHNICAL FIELD

The present invention relates to an agent for conferring resistance containing a lectin as an effective component, whereby resistance to external stimuli is conferred to cultured animal cells and various tissues in the living bodies, as well as to a method and kit which employ the resistance-conferring agent to confer such resistance to external stimuli.

BACKGROUND ART

In recent years, autogenic or allogenic transplantation of cultured mesenchymal stem cells, osteoblasts, chondrocytes, periodontal cells, dental pulp cells and the like has been reported to be effective for repairing loss of cartilage, bone and/or periodontium or dental pulp caused by disorders of cartilage, bone or dental conditions such as bone fracture, osteoarthritis, cartilage injury, myeloma, periodontal disease, pulpitis and the like. However, transplantation of such cultured cells can lead to damage or destruction of the transplanted cells due to the surrounding tissue or inflammatory or immune cell activation, in many cases resulting in deciduation, absorption or necrosis of the transplanted tissue. Since dental pulp cells, having a minimal extracellular matrix, are particularly susceptible to peeling by mechanical stimuli, it has been difficult to provide cultured dental pulp cells for transplantation.

In order to facilitate fixation of transplanted tissue into surrounding tissue and thus promote repair of the tissue, it is important for the cells of the transplanted tissue to maintain resistance against external stimuli from the surrounding tissue or from inflammatory or immune cell activation, and specifically against mechanical stimuli and/or proteolytic reactions. In addition, increased resistance to external stimulus of immature cells and/or tissues in repairing or regenerating mesenchyme, bone, cartilage, periodontum or dental pulp has been found to be effective for treatment of various bone, cartilage or periodontal or dental pulp diseases.

Transplant tissues have been therefore encapsulated in glass fibers or in immunoisolation membranes. For example, insulin-producing mouse Langerhans cells are usually encapsulated in an immunoisolation membrane for transplant into diabetes patients. However, artificial materials are disadvantageous in that they can provoke immunological rejection and have low adhesion strength. Immunoisolation membranes are problematic because they require laborious synthesis of high-strength polymer films that allow adequate passage of beneficial proteins secreted by cells, as well as enzymes and nutrients, without permitting passage of immune complement proteins (PNE, Vol. 45, No. 13(2000), pp. 2139–2141, 2171–2178, 2307–2312). Although other strategies have included the use of immunosuppressants, extracorporeal circulation of the blood through artificial organs made of cultured cells, and transplantation to locations with low immune cell-induced rejection while avoiding the deficient or impaired sites which are most prone to immune response, such strategies have drawbacks including side-effects of immunosuppressant, the burden of extracorporeal circulation on patients, and the remaining of deficient or impaired sites. It has therefore been desired to confer resistance to the actual cells and/or tissues.

Lectins are ligand-specific sugar-binding proteins with bivalent or more valence found mainly in plants and animals, having activities of agglutinating various types of animal and plant cells and precipitating polysaccharides or complex carbohydrates. Some lectins, such as concanavalin A, are known to exhibit activity for promoting juvenilization of T cells. The effects of different lectins on differentiation and proliferation of chondrocytes have been studied, and it has been reported that lectins (such as concanavalin A) with affinity for α-D-mannose residues and α-D-glucose residues powerfully promote differentiation of chondrocytes, based on increased proteoglycan synthesis (Yan et al., J. Biol. Chem., Vol. 265, pp. 10125–10131, 1990). Nevertheless, it has not been known whether concanavalin A and other lectins can confer resistance against external stimulus to animal cells, particularly cultured cells, and/or various types of tissue in the living bodies.

DISCLOSURE OF THE INVENTION

It is therefore an object of the present invention to provide an agent that confers resistance to external stimulus, as well as a method of conferring resistance against external stimulus to animal cells and/or tissues.

As a result of much diligent research directed toward conferring resistance against external stimulus to cultured mesenchymal stem cells, osteoblasts, chondrocytes, periodontal cells, dental pulp cells, fibroblasts, epithelial cells, myoblasts and the like for transplantation, the present inventors have discovered that lectins are capable of conferring resistance against external stimulus to such cells.

The invention therefore provides an agent for conferring resistance containing a lectin as an effective component, whereby resistance to external stimuli is conferred to cultured animal cells.

The invention further provides a method of conferring resistance against external stimulus to animal cells and/or tissues which comprises treating the cells and/or tissues with lectins. According to this method, the lectin treatment may involve direct application of a lectin to the cells and/or tissues, or when the cells are cultured cells, the lectin has been added in a culture medium.

According to the invention, the external stimulus of the term "resistance to external stimulus" is a stimulus on transplanted tissue by the tissue surrounding the transplant site or by inflammatory or immune cells against the graft, and specifically it is a mechanical stimulus and/or proteolytic reaction.

The animal cells to be treated with the resistance-conferring agent of the invention may be any type of animal cells, but mesenchymal stem cells, osteoblasts, chondrocytes, periodontal cells, dental pulp cells, fibroblasts, epithelial cells and myoblasts are preferred. The cells are also preferably from a mammal, such as a rodent (mouse, rat, rabbit), dog, monkey, cow, goat, sheep or human, with human-derived cells being most preferred.

According to the invention, lectins which may be used as an agent for conferring resistance to external stimulus include any lectins having an effect of conferring resistance against external stimulus to animal cells, such as animal-derived lectins or plant-derived lectins, among which concanavalin A (ConA), phytohemagglutinin E (PHA-E), phytohemagglutinin P (PHA-P) and wheat germ agglutinin (WGA) are preferred, and ConA or PHA-E are especially preferred. The concentration of the lectin used will differ depending on the type of lectin and/or the cells to be treated, and may be 0.01–1000 μg/mL, preferably 0.1–100 μg/mL, more preferably 1–20 μg/mL and most preferably 5–10 μg/mL, whether by addition to the medium or by a single treatment. The time for treatment of the animal cells with the lectin will also differ depending on the type and concentration of the lectin used and the cells to be treated, and it may be from 1 minute to 10 days or longer, and preferably 1–48 hours, such as 24 hours. When using ConA or PHA-E, the cells may be treated with the ConA or PHA-E in a single treatment, but alternatively they may be incubated over a period of a few minutes to several days in the presence of the ConA or PHA-E. When the purpose includes simultaneously promoting differentiation of cartilage, the cells may be subjected to prolonged culturing in the presence of a low concentration of ConA or PHA-E. Culturing will be performed for a shorter period when higher concentrations of ConA or PHA-P are desired.

Animal Cells

Examples of animal cells to be conferred resistance to external stimulus in the invention include, as mentioned above, mesenchymal stem cells, osteoblasts, chondrocytes, periodontal cells, dental pulp cells, fibroblasts, epithelial cells and myoblasts.

Mesenchymal stem cells may be obtained from any bone marrow or periosteal tissue containing such cells, but are preferably obtained from the femur, tibia or pelvis (ilium), as large amounts of cells can be readily obtained from these sites. Mesenchymal stem cells can also be conveniently obtained from the pelvis and tibia of non-human mammals.

Osteoblasts can be obtained in vitro by culturing mesenchymal stem cells in medium suitable for bone differentiation, such as the medium described by M. F. Pittenger et al. (see below), to induce bone differentiation.

Chondrocytes can be obtained from cartilage cells of cartilage tissue from, for example, auricular cartilage, costal cartilage, articular cartilage, intervertebral cartilage or tracheal cartilage. Articular cartilage includes cartilage from the temporomandibular joint, brachial joint, elbow joint, shoulder joint, wrist joint, thigh joint, hip joint or ankle joint. Chondrocytes can also be obtained in vitro by transferring of mesenchymal stem cells into a centrifugal tube culturing system, suspended culturing system, agarose culturing system or alginic acid culturing system, and inducing chondrocytes in a medium suitable for inducing cartilage differentiation, such as the medium described by M. F. Pittenger et al., Science 284, pp. 143–147, 1999.

Periodontal cells can be obtained from extracted teeth according to the method described by Shimazu et al. (Shimazu et al., J. Dent. Res. 78, pp. 1791–1799, 1999).

Dental pulp cells can be obtained from dental pulp according to the method described by Yokose et al. (Yokose et al., Calcif. Tissue Int. 66, pp. 139–144, 2000). Specifically, dental pulp cells may be obtained by a septically extracting dental pulp tissue from a tooth, treating it with an enzyme (such as collagenase) and recovering the released cells by centrifugal separation.

The method of obtaining mesenchymal stem cells from bone marrow may be any publicly known method, such as one commonly employed in medical care. A laboratory method may be employed to obtain cells from the bone marrow of a non-human mammal, whereby the ends of the bone (femur, tibia) are cut off, the introsseous tissue is washed with medium suitable for culturing of mesenchymal stem cells, and the mesenchymal stem cells are obtained from the washed culture solution. A method for obtaining mesenchymal stem cells is described in detail below.

(1) The ends of a rabbit femur and tibia are cut off. The bone marrow is then washed with a medium such as DMEM medium, with optional addition of antibiotics (for example, penicillin, streptomycin, etc.) and heparin.

(2) In the case of human ilial or alveolar bone, fluid is obtained from the bone marrow of the ilium or alveolar bone.

(3) The washing medium or the bone marrow fluid is centrifuged at 300×g for about 3 minutes, the agglutinated lump is removed as a precipitate, and the cells in the supernatant are seeded in a tissue culturing plate. After 3 days of culturing, the adhering cells are counted as the mesenchymal stem cells.

(4) Culturing is then performed in a suitable medium (for example, 10% FBS-containing DMEM medium).

A publicly known method in the field may be employed to obtain the stem cells from the periosteum [M. Iwasaki et al., Endocrinology 132, 1603–1608 (1993); J. Fang & B. K. Hall, Developmental Biol. 180, 701–712 (1996); S. Bahrami et al., The Anatomical Record 259, 124–130 (2000)].

Chondrocytes can also be obtained from various types of animal cartilage tissue by a publicly known method, such as from rabbit costal cartilage growth plate by the method of Kato et al. (Kato et al., J. Cell Biol., Vol. 100, pp. 477–485, 1985), using proteases and collagenases for treatment to obtain the chondrocytes.

The obtained mesenchymal stem cells, osteoblasts, chondrocytes, periodontal cells, dental pulp cells, fibroblasts, epithelial cells or myoblasts maybe directly seeded for culturing, but in most cases they will be used after culturing for about 10–20 days in a suitable medium. The cells may also be cryopreserved.

Method for Conferring Resistance against External Stimulus to Animal Cells

Cells obtained in the manner described above are conferred resistance to external stimuli in the following manner.

(1) The cells are seeded into medium suitable for culturing of the cells, such as 1.0% FBS-containing DMEM medium, at 3000 cells/cm$^2$, for example, and are allowed to grow to approximate confluence. The culturing may be carried out under any conditions suitable for animal cell culturing, but for mammalian cells it is preferably conducted at 37° C. in the presence of 5% $CO_2$.

(2) A lectin is then added to the medium at a desired concentration, such as 1–50 μg/mL, and culturing is continued for 24 hours.

(3) The cells (cell layer) are rinsed with an appropriate solution such as PBS, and then stationed in the medium.

Cells thus treated exhibit marked resistance against external stimuli (for example, mechanical stimuli and/or proteolytic reactions). Resistance to external stimulus can be conferred to various biological tissues by using different lectins for cells in the body.

The present invention will now be explained in greater detail through examples, with the understanding that the examples are not limitative on the invention.

BEST MODE FOR CARRYING OUT THE INVENTION

EXAMPLES

Example 1

Obtaining Animal Cells

1) Obtaining Mesenchymal Stem Cells from Bone Marrow

After extracting femoral and tibial bone from 4-week-old rabbits and removing the muscle and ligaments, the ends thereof were cut off. The intraosseous tissue was then washed with DMEM medium (containing 32 units/mL penicillin, 50 $\mu$g/mL streptomycin and 6000 units/mL heparin). The washing medium was centrifuged at 300×g for 3 minutes, and the agglutinated lump was removed as a precipitate. The cells in the supernatant were seeded in a tissue culturing plate and cultured for 3 days, and the adhering cells were counted as the mesenchymal stem cells.

2) Obtaining Mesenchymal Stem Cells from Ilium

After extracting ilial bone from 4-week-old rabbits, the bone marrow fluid was removed from the ilial bone and centrifuged at 300×g for 3 minutes, and the agglutinated lump was removed as a precipitate. The cells in the supernatant were seeded in a tissue culturing plate and cultured for 3 days, and the adhering cells were counted as the mesenchymal stem cells, in the same manner as above.

3) Obtaining Periodontal Cells

Periodontal cells were obtained from extracted teeth according to the method of Shimazu et al.

4) Obtaining Dental Pulp Cells

Dental pulp cells were obtained by aseptically extracting dental pulp tissue from mandibular incisors of 8-week-old Wistar rats, adding 3 ml of enzyme solution (PBS containing 0.1% collagenase, 0.05% trypsin and 4 mM EDTA) to the dental pulp tissue, treating them at 37° C. for 20 minutes and recovering the supernatant. This procedure was repeated 6 times. The recovered cells were then cultured in a 10 cm dish using 10% FBS-containing DMEM medium. Upon reaching 70% confluence, the cells were treated at 37° C. for 5 minutes in PBS containing 0.05% trypsin and 0.02% EDTA, and the isolated cells were recovered and counted as the dental pulp cells.

5) Obtaining Chondrocytes

Rabbit chondrocytes were used. The costal cartilage growth plates were surgically extracted from 4-week-old New Zealand white rabbits. The costal cartilage growth plates were then subjected to trypsin and collagenase treatment according to the method of Kato et al. to separate the chondrocytes. This method yielded approximately $4\times10^6$ chondrocytes per rabbit.

6) Obtaining Osteoblasts

Mesenchymal stem cells obtained according to 1) above were transferred to bone differentiation-inducing medium having the following composition.

Bone Differentiation-Inducing Medium

αMEM medium 100 nM dexamethasone 10 mM β-glycerol phosphate

50 $\mu$g/ml ascorbic acid 2-phosphate

The mesenchymal stem cells were cultured in the aforementioned medium at 37° C. in the presence of 5% $CO_2$. Culturing was conducted for 12 days with exchange of the medium every 2 days, to induce ossification and obtain osteoblasts.

Example 2

Examining Resistance Against External Stimuli

1) Resistance Against Proteolytic Reaction (Mesenchymal Stem Cells)

Figure 1:
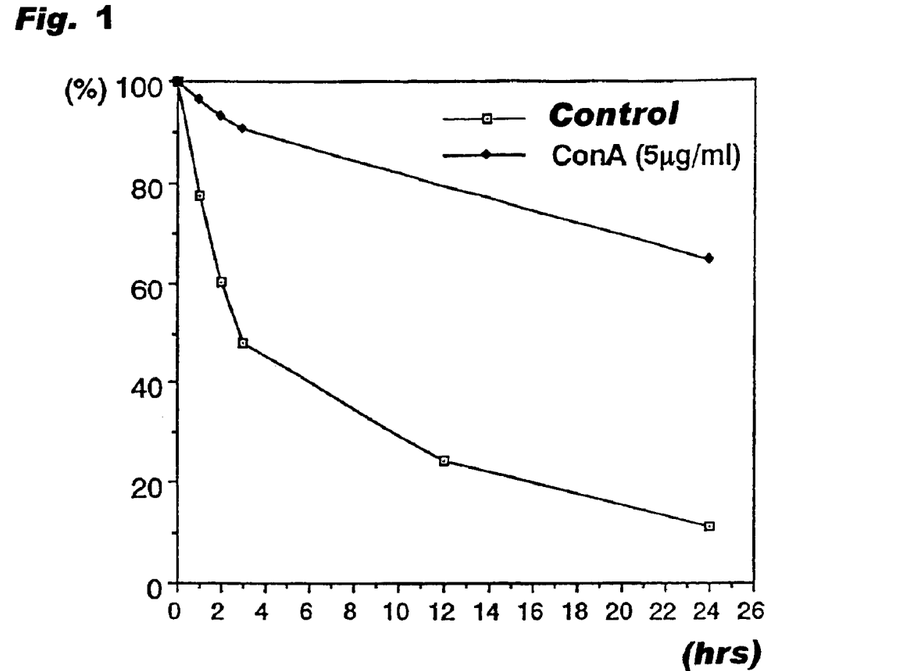
FIG. 1 is a graph showing that resistance against proteolytic reaction was conferred to mesenchymal stem cells by ConA treatment.

Mesenchymal stem cells obtained in Example 1 were seeded onto a culturing plate (10% FBS-containing DMEM medium) at a density of 3000 cells/cm² and cultured for 7–10 days at 37° C. in the presence of 5% $CO_2$ to confluence. Concanavalin A (ConA) was added as a lectin at 5 $\mu$g/mL and culturing was continued for 24 hours. A control with no lectin addition was also separately cultured for 24 hours. The cultured cell layer was rinsed with PBS and then incubated for 1–24 hours upon addition of 1) DMEM medium containing 0.25% trypsin/4 mM EDTA, 2) DMEM medium containing 0.1% collagenase (Type IA, Sigma) or 3) DMEM medium containing 2 mg/mL pronase. The number of cells released and isolated from the cell layer by proteolytic treatment was counted using a Coulter counter. FIG. 1 shows the results for the ConA-added group in 0.1% collagenase-containing medium and the control group. The addition of ConA at 5 $\mu$g/mL clearly inhibited dispersion of cells by 0.1% collagenase (FIG. 1). Similar results were also observed after 24 hours of incubation in the 0.25% trypsin/4 mM EDTA-added medium and 2 mg/mL pronase-added medium.

Figure 2:
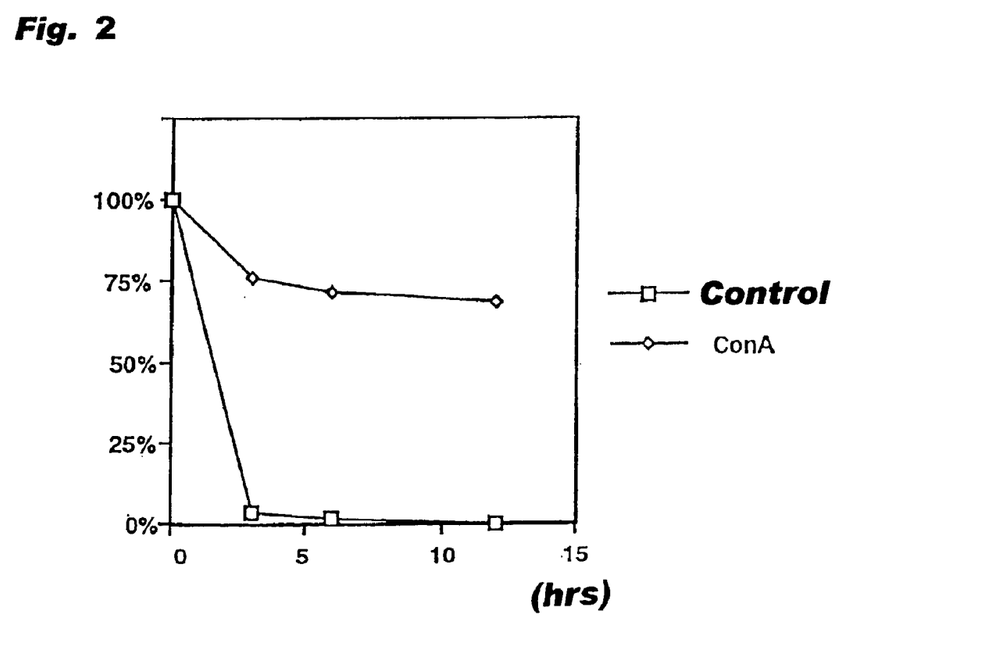
FIG. 2 is a graph showing that resistance against proteolytic reaction was conferred to mesenchymal stem cells by ConA treatment.

In order to examine the effect of ConA under more stringent conditions, 10 $\mu$g/mL ConA was added to the mesenchymal stem cells prior to 24 hours of culturing, and the resultant cell layer was incubated for 1–12 hours with further addition of DMEM medium containing 0.25% trypsin+1 mM EDTA+0.1% collagenase. The released cells were then counted with a Coulter counter. As a result, release of cells in the ConA-treated group was notably inhibited, whereas virtually all of the cells were released in the control group (FIG. 2).

Upon examining the resistance-conferring effects with different concentrations of ConA, a resistance-conferring effect by ConA on mesenchymal stem cells was observed from 1 µg/mL and reached an approximate maximum at 20 µg/mL.

2) Resistance Against Proteolytic Reaction (Dental Pulp Cells)

Dental pulp cells obtained in Example 1 were seeded in a 6-well plate with DMEM medium containing 10% FBS and 50 µg/mL ascorbic acid, at a density of $2 \times 10^4$ cells/cm$^2$. When the cells reached 90% confluence, the culture solution was exchanged with DMEM medium containing 0.5% FBS and 50 µg/mL ascorbic acid for 24 hours of preculturing. After exchange with the same culture solution, ConA was added at various concentrations (1, 5, 10 µg/mL) for 24 hours of treatment. The cells were then rinsed with PBS, DMEM medium containing 0.2% collagenase was added, the cells which became suspended each hour were collected and counted with a Coulter counter, and the proportion of cells released from the cell layer was calculated.

Figure 3:
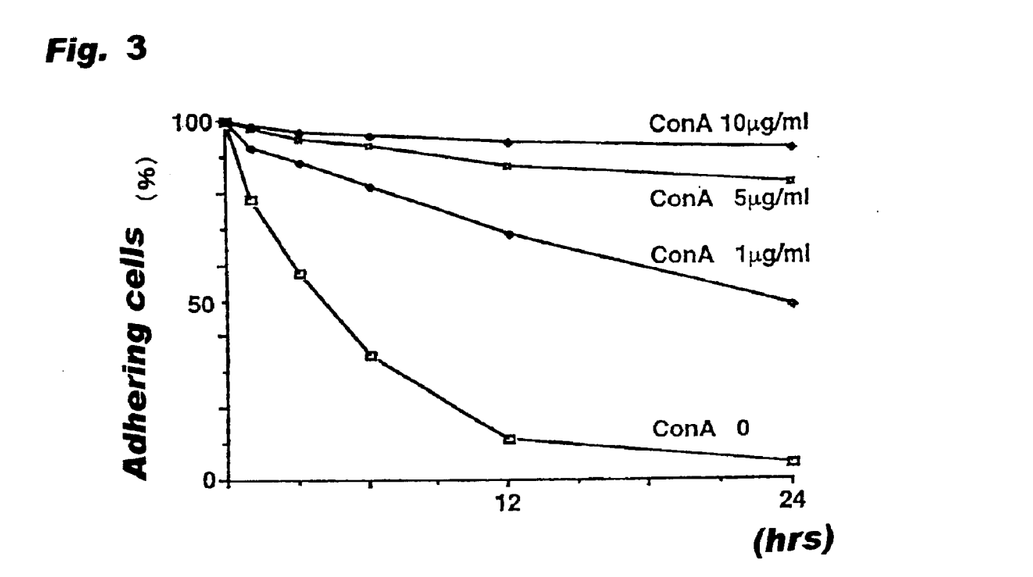
FIG. 3 is a graph showing that resistance against collagenase treatment was conferred to dental pulp cells by ConA treatment.

As a result, dispersion of cells due to collagenase activity in the ConA-treated groups (1, 5, 10 µg/mL) was notably inhibited, whereas virtually all of the cells were released in the non-ConA-treated control group (FIG. 3).

Similar experiments were conducted with the chondrocytes, periodontal cells and osteoblasts prepared from mesenchymal stem cells obtained in Example 1. As a result, ConA treatment at 5 µg/mL and 10 µg/mL was found to notably inhibit release of the respective cells from their cell layers induced by the proteolytic enzymes trypsin, collagenase and pronase. This demonstrated that ConA treatment had conferred to the cells resistance against proteolytic reaction. The results are summarized in the following table.

TABLE 1

| Conferred resistance against proteolytic reaction | | | | | | |
|---|---|---|---|---|---|---|
| | | Mesenchymal stem cells | Chondro-cytes | Oseto-blasts | Periodontal cells | Pulp cells |
| Control group | | − | − | − | − | − |
| ConA-added group | 5 µg/ml | ++ | ++ | ++ | ++ | ++ |
| | 10 µg/ml | +++ | +++ | +++ | +++ | +++ |

3) Conferring Resistance Against Mechanical Stimuli

Following the procedure described in 2) above, dental pulp cells were treated with ConA (10 µg/ml, 24 hours) and the cell layer was rinsed with PBS. The cells in DMEM medium were mechanically shaken for 5 minutes using a shaker (Water Bath Shaker, Personal-11, TAITEC) at 80 shakes per minute, and the number of cells detached from the culturing plate was counted. As a result, the cells detached from the culturing plate in the control group, whereas almost none of the cells detached in the ConA-treated group. The results are shown in Table 2 below.

TABLE 2

| Resistance against mechanical stimuli | |
|---|---|
| | Resistance |
| Control group | − |
| ConA-treated group (10 µg/ml) | ++ |

4) Resistance Against Extracellular Matrix Proteoglycan Degradation

Figure 4:
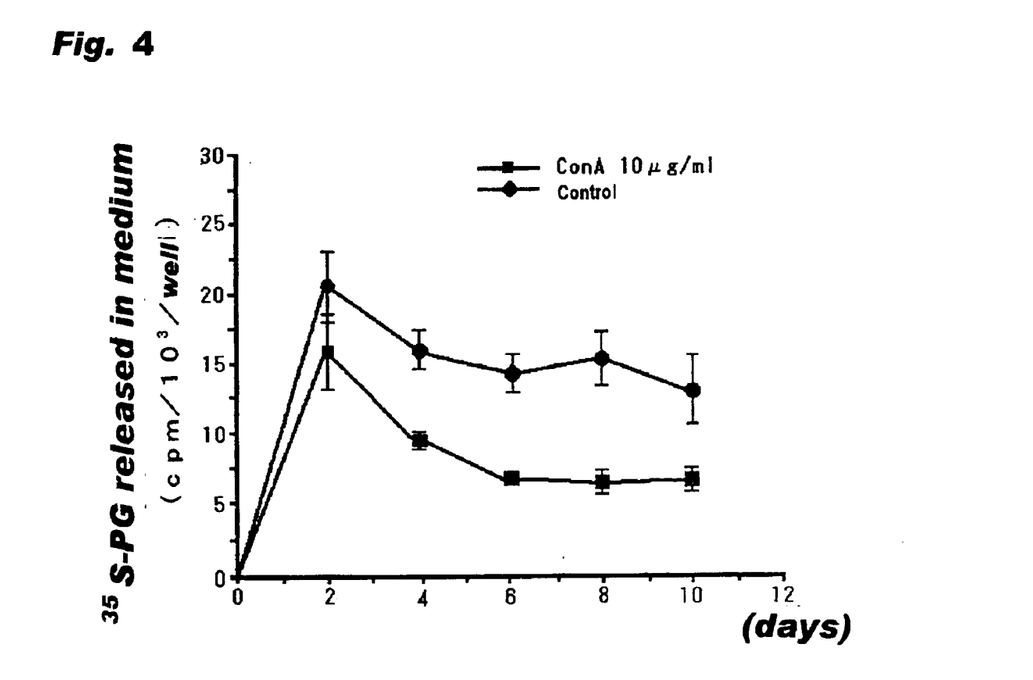
FIG. 4 is a graph showing that ConA-treatment inhibited degradation of proteoglycan, chondrocyte extracellular matrix, and release into medium.

The resistance against extracellular matrix proteoglycan degradation was tested according to the method of Shimazu et al. (Arthritis and Rheumatism, Vol. 36, pp. 247–253), by measuring release of [$^{35}$S]-labeled proteoglycan. Rabbit costal cartilage-derived chondrocytes were cultured to confluence in the same manner as Example 2-1). The confluent cells were incubated for 24 hours with [$^{35}$S]-sulfuric acid for [$^{35}$S] labeling of proteoglycan, the major component of the chondrocyte matrix. The cell layer was thoroughly washed with serum-free medium (PBS) and then incubated at 37° C. either in the presence of 10 µg/mL ConA (ConA-treated group) or without (control group), and a portion of the medium was sampled after 2, 4, 6, 8 and 10 days to measure the [$^{35}$S]-proteoglycan degraded and released into the medium. The results clearly demonstrated that ConA treatment inhibited degradation and release of extracellular matrix proteoglycan into the medium (FIG. 4).

Example 3

Examining Resistance in Vivo

Figure 5:
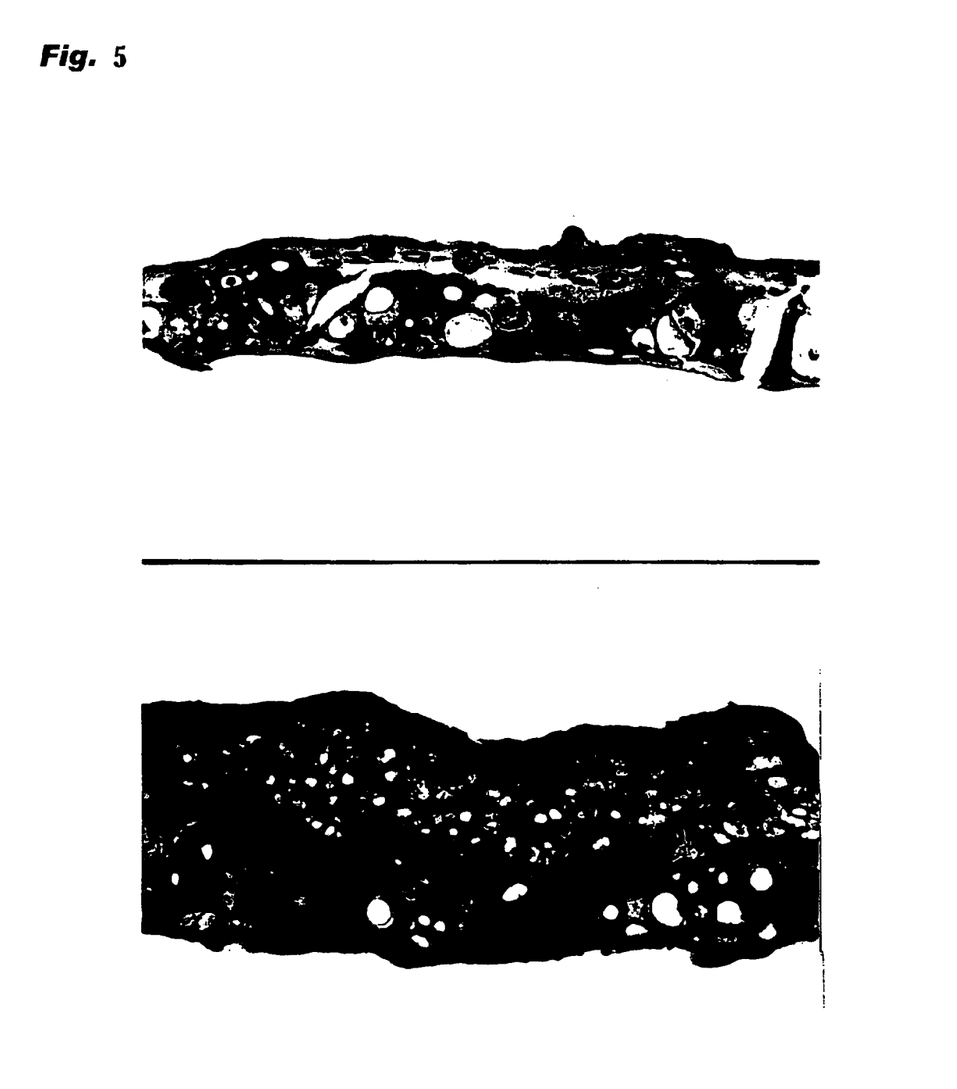
FIG. 5 is a micrograph showing that ConA-treatment enhanced transplant tissue fixation in a cartilage graft.

Rabbit chondrocytes ($8 \times 10^4$ cells) obtained in Example 1 were seeded in MEM medium containing 1 mL 10% FBS and 50 µg/mL ascorbic acid, and were cultured for 3 weeks in a centrifugal tube culturing system at 37° C. in the presence of 5% $CO_2$. ConA was added twice at 10 µg/mL during the culturing period. ConA inhibits cell growth, and as a result no change in tissue volume was found during the culturing. The cartilage tissue obtained by the culturing was transplanted under the skin of syngeneic rabbits and the transplanted tissue was extracted after 3 weeks. Tissue sections were prepared and dyed with toluidine blue for observation of the transplanted cartilage tissue. Several layers of cartilage and bone tissue were observed in the control group, while the tissue thickness increased by about 2-fold in the ConA-added group (FIG. 5). This indicated that ConA treatment had conferred resistance against external stimulus to transplanted cartilage cells/tissue, thereby enhancing fixation of transplanted tissue in grafts.

Example 4

Examining Different Lectins

Other lectins were examined to determine whether they are able to confer resistance against external stimulus to animal cells in the same manner as ConA. Phytohemagglutinin E (PHA-E) and wheat germ agglutinin (WGA) were used as lectins other than ConA for this example.

Figure 6:
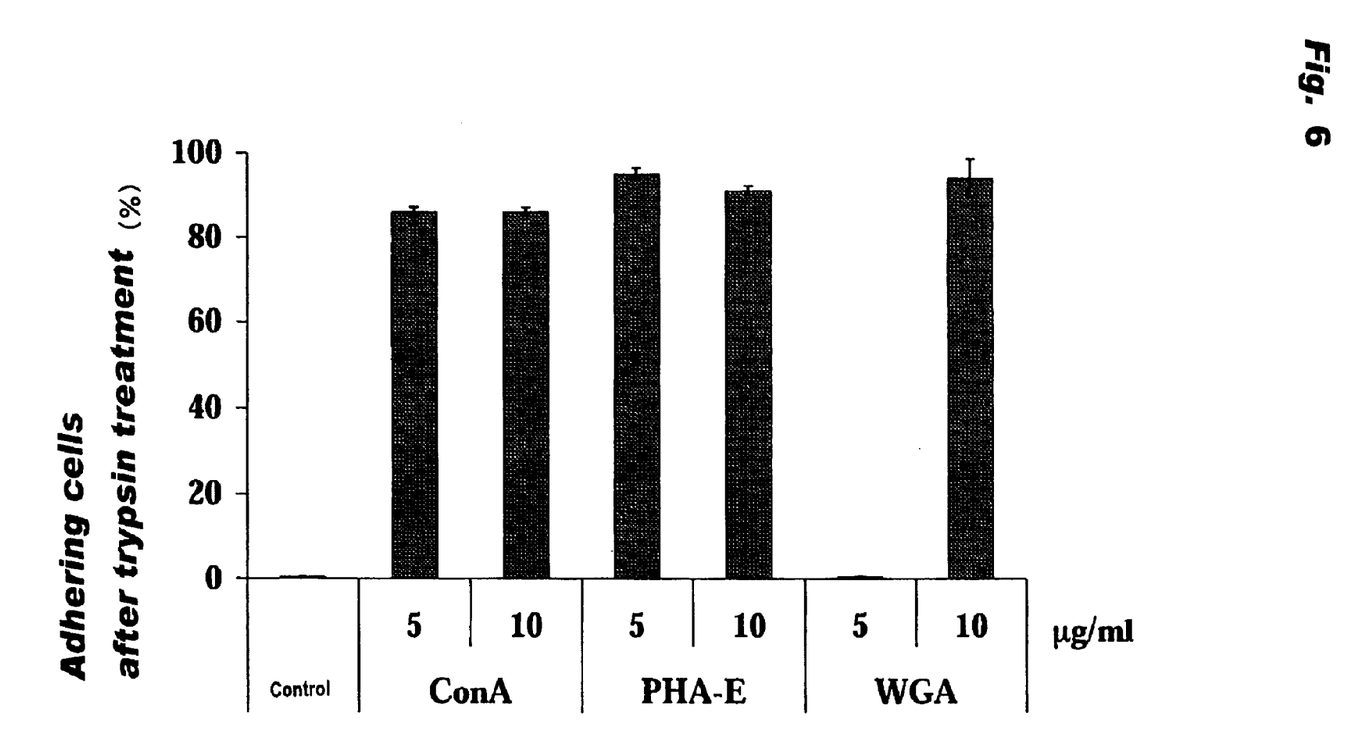
FIG. 6 is a graph showing effects of various lectins for conferring resistance against proteolytic reaction.

Mouse bone marrow-derived mesenchymal cells were obtained according to the method used in Example 1—1). The cells were seeded in the same manner as Example 2 and cultured in 10% FBS-containing αMEM medium. Different lectins were then added to the mouse mesenchymal cells at 5 µg/mL or 10 µg/mL prior to incubation at 37° C. for 3 hours. A non-lectin-treated group was used as a control. After rinsing the cell layer with PBS, 0.25% trypsin+1 mM EDTA was added and incubation was continued at 37° C. for 15 minutes. The number of cells remaining in the cell layer was counted with a Coulter counter in the same manner as Example 2. As a result, virtually all of the cells were released in the control group, whereas release of the cells in the ConA-treated group was notably inhibited with PHA-E treatment at 5 µg/mL and 10 µg/mL (FIG. 6). Cell release occurred with WGA treatment at 5 µg/mL, but cell release was inhibited at 10 µg/mL. These results indicated that PHA-E, like ConA, also exhibits a marked effect.

Example 5

Examining Lectin Concentration

The resistance-conferring effects of ConA and PHA-E, whose effect was confirmed in Example 4, were further examined at various concentrations.

Figure 7:
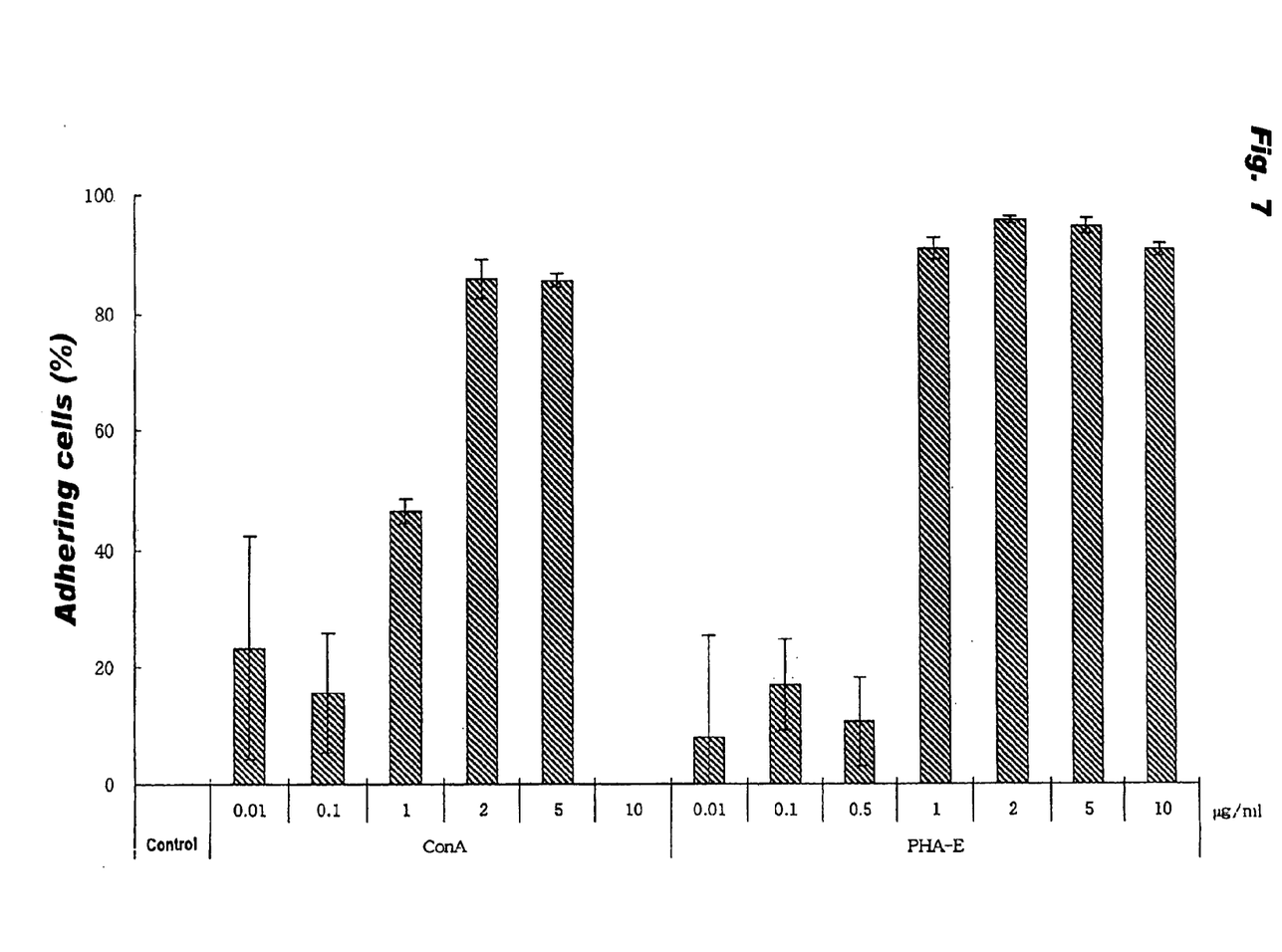
FIG. 7 is a graph showing the effects of ConA and PHA-E at different concentrations.

Rabbit bone marrow-derived mesenchymal cells obtained in Example 1 were cultured in 10% FBS-containing αMEM medium, ConA or PHA-E was added at various concentrations (0.01, 0.1, 0.5, 1, 2, 5 and 10 µg/mL) before the cells reached confluence, and the cells were incubated at 37° C. for 3 hours. After rinsing the cell layer with PBS, 0.25% trypsin+1 mM EDTA was added and incubation was continued at 37° C. for 15 minutes. The number of cells remaining in the cell layer was counted with a Coulter counter in the same manner as Example 2. The results demonstrated effects by both ConA and PHA-E at concentrations as low as 0.01–0.1 µg/mL, and showed that PHA-E exhibits a stronger effect at lower concentrations than ConA (FIG. 7).

Example 6

Examining the Time of Lectin Treatment

The time (treatment time) required for ConA and PHA-E to confer protease resistance to cells was examined.

Figure 8:
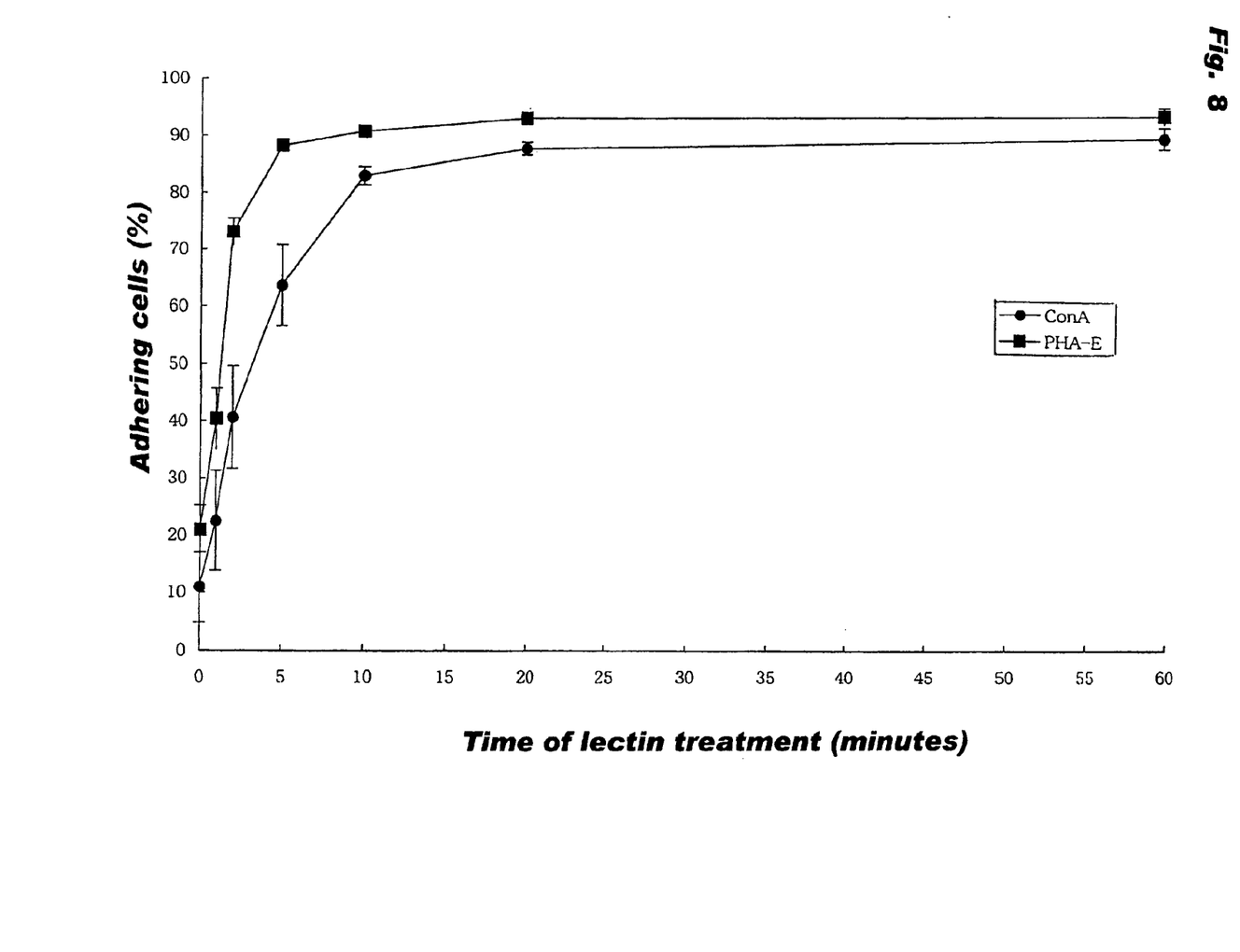
FIG. 8 is a graph showing the treatment time required for ConA and PHA-E to confer resistance against proteolytic reaction.

Mouse bone marrow-derived mesenchymal stem cells were cultured in the same manner as Example 4. ConA and PHA-E were added at a concentration of 5 µg/mL at 60, 20, 10, 5, 2, 1 and 0 minutes before trypsin treatment (0.25% trypsin+1 mM EDTA). Lectin and trypsin were added simultaneously at 0 minutes. After trypsin treatment, the number of cells remaining in the cell layer was counted with a Coulter counter. The results indicated that treatment with lectin for 10–20 minutes conferred to the cells almost maximum resistance against protease (FIG. 8).

Example 7

Examining Effects Against Different Proteases

The effects of ConA and PHA-E against proteolytic reactions by different proteases were examined.

Figure 9:
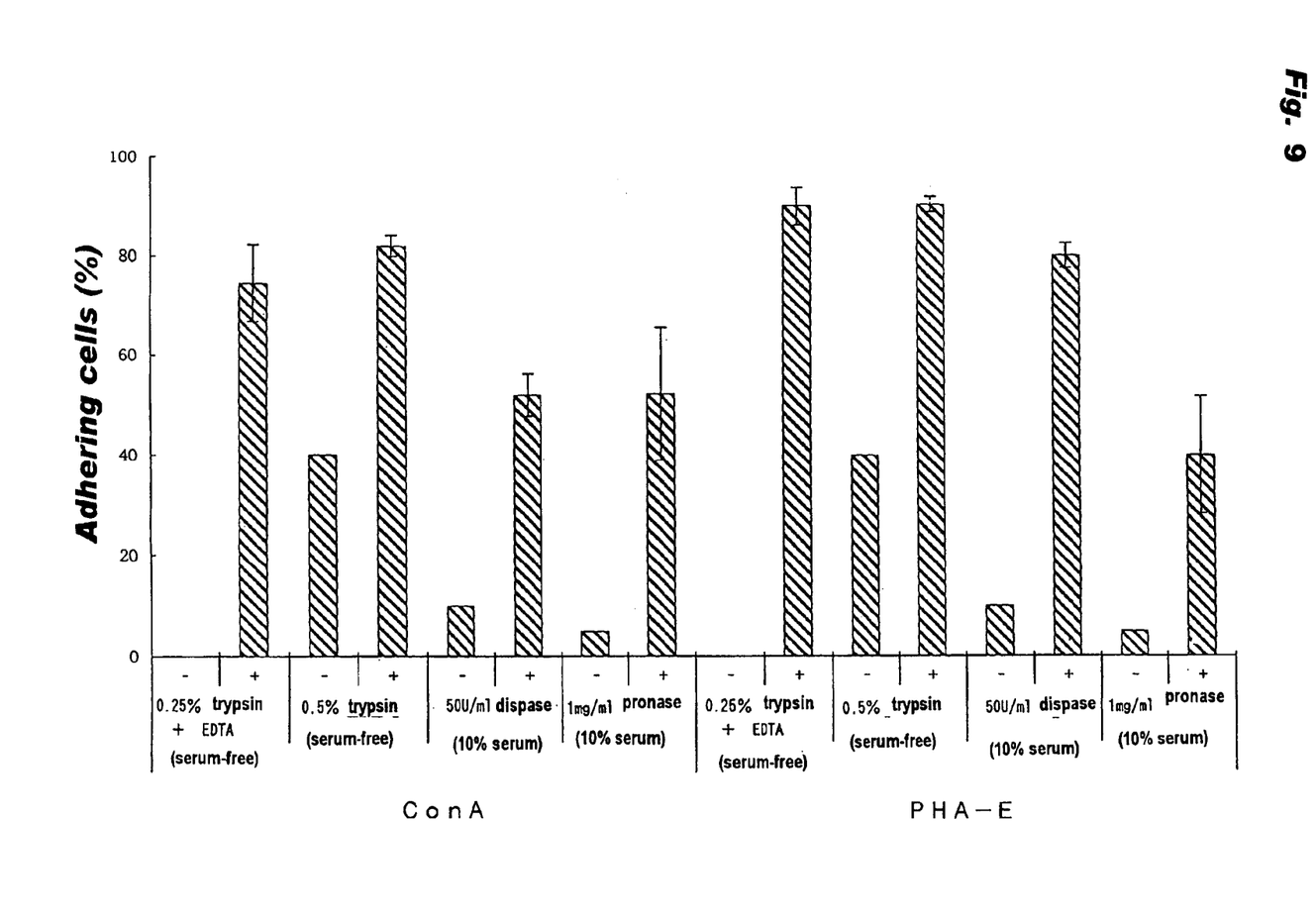
FIG. 9 is a graph showing the ability of ConA and PHA-E to confer resistance against proteolytic reaction by different proteases.

Mouse bone marrow-derived mesenchymal stem cells were cultured in the same manner as Example 4. ConA or PHA-E was added as a lectin at a concentration of 5 µg/mL, and incubation was performed at 37° C. for 20 minutes. After rinsing the cell layer with PBS, serum (10% FBS)—containing αMEM medium or serum-free αMEM medium was added. As proteases there were added 0.25% trypsin (tri)+1 mM EDTA or 0.5% trypsin (tri) to the serum-free αMEM medium and 50 U/mL dispase or 1 mg/mL pronase to the serum-containing αMEM medium, and incubation was continued at 37° C. for 15 minutes. The number of cells remaining in the cell layer was counted with a Coulter counter in the same manner as Example 2. As a result, almost all of the cells were released in the medium of the lectin-untreated group (−), whereas in the lectin-treated groups (+), ConA and PHA-E notably inhibited release of the cells (FIG. 9). This demonstrated that ConA and PHA-E are effective against proteolytic reaction of not only a specific protease but also several other proteases.

Example 8

Examining Different Animal Cells

It was examined whether lectins can confer resistance to different cells and cell lines including fibroblast cell lines, epithelial cell lines and myoblast cell lines.

(1) Cells

Effects of lectins on cells obtained and cultured from tissue (non-cell lines) as well as various known cell lines were investigated. The cells and cell lines used are listed below.

| Cells (non-cell lines) | Morphology |
| --- | --- |
| Rabbit bone marrow cells (BMC) | fibroblasts |
| Rat pulp cells | fibroblasts |
| Rat periosteal cells | fibroblasts |
| Rat diaphragm cells | fibroblasts |
| Human gingival cells | fibroblasts |

| Cell lines | Source |
| --- | --- |
| Fibroblast cell lines | |
| 10T1/2 | murine, C3H, fetal |
| MC3T3-G2/PA6 | murine, C57BL/6 |
| MC3T3-E1 | murine, C57BL/6 |
| Epithelial cell lines | |
| BCE | bovine, corneal |
| ATDC5 | murine, 129 |
| HBL-100 | human, mammary |
| COS-7 | simian, renal |
| HeLa | human, uterine |
| HepG2 | human, hepatic |
| Myoblast cell line | |
| C2C12 | murine, C3H, muscular |

(2) Experiment

The cells were seeded and cultured as Example 4. ConA or PHA-E was added as a lectin at concentrations of 1, 5 and 10 µg/mL, and the cells were incubated at 37° C. for 20 minutes. After rinsing the cell layer with PBS, 0.25% trypsin (tri)+1 mM EDTA was added and incubation was continued at 37° C. for 15 minutes. The number of cells remaining in the cell layer was counted with a Coulter counter in the same manner as Example 2.

(3) Results

Figure 10:
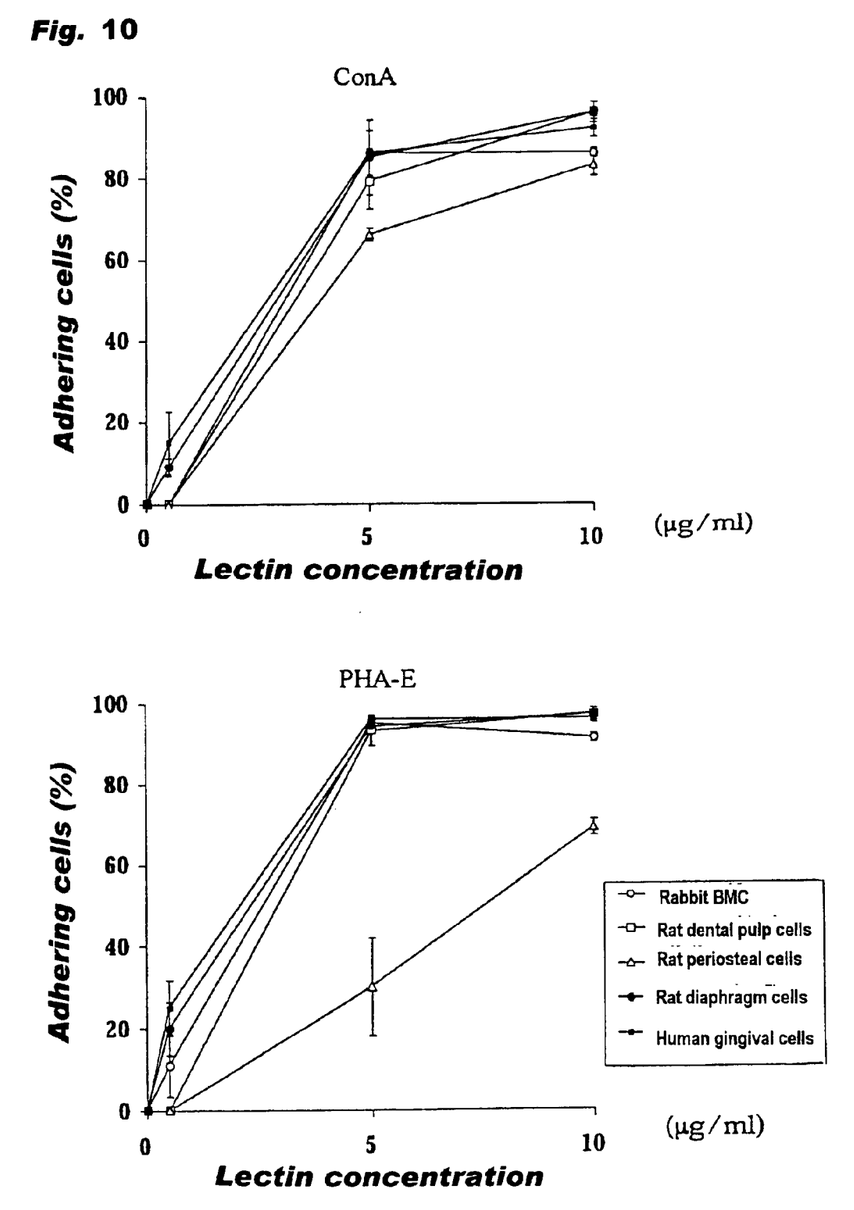
FIG. 10 is a graph showing that resistance against proteolytic reaction was conferred to fibroblast cells (non-cell lines) by ConA and PHA-E.
Figure 11:
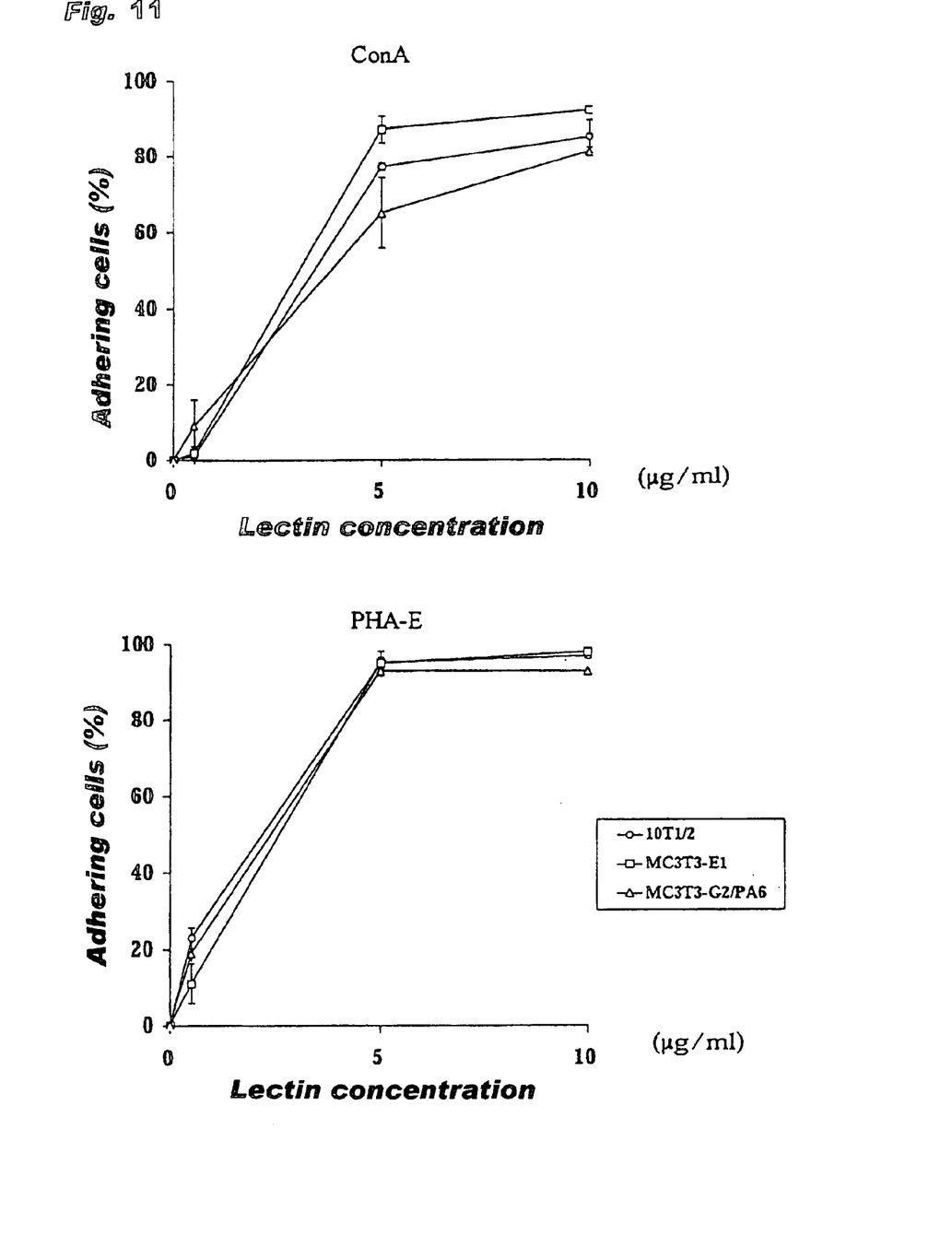
FIG. 11 is a graph showing that resistance against proteolytic reaction was conferred to fibroblast cell lines by ConA and PHA-E.
Figure 12:
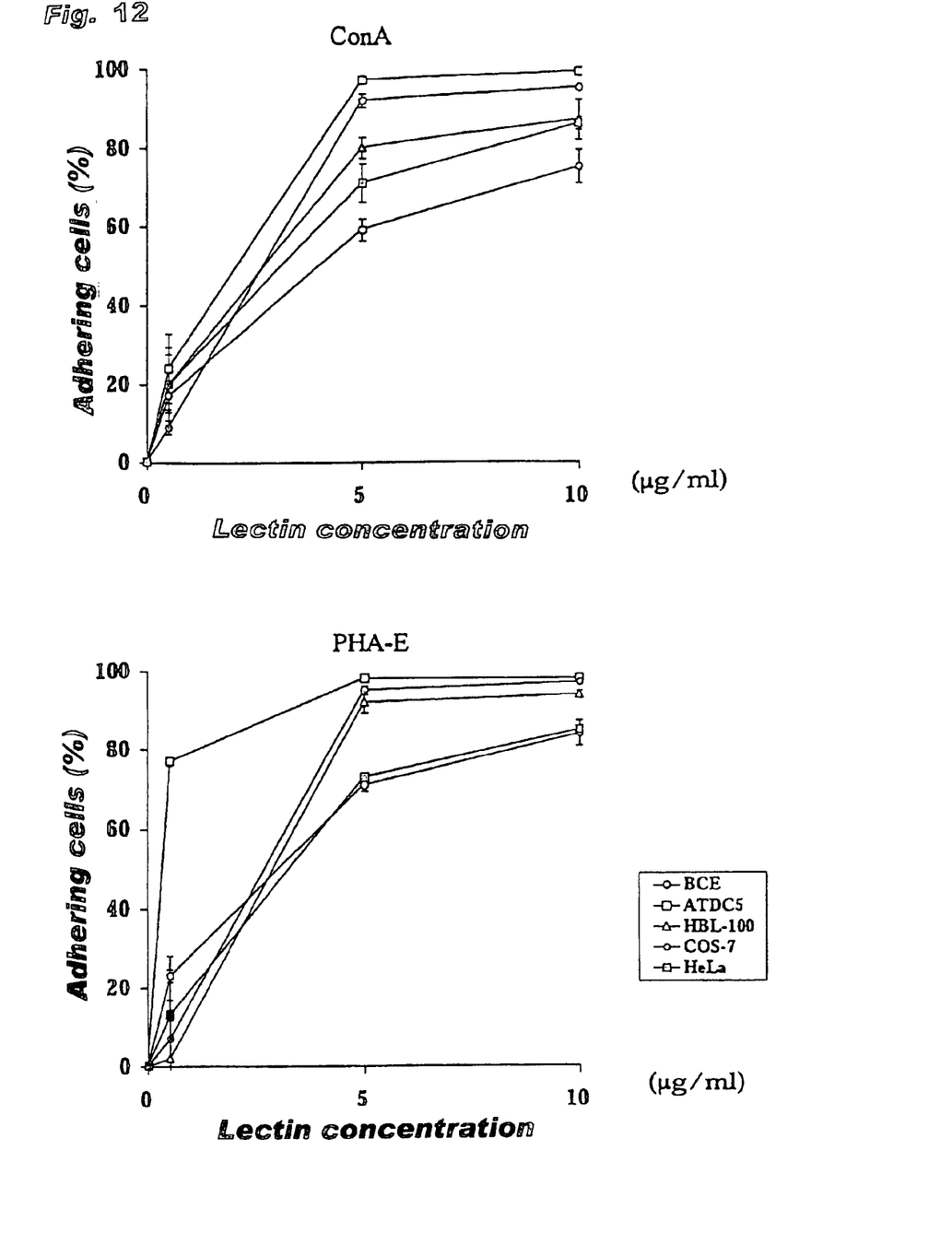
FIG. 12 is a graph showing that resistance against proteolytic reaction was conferred to epithelial cell lines by ConA and PHA-E.
Figure 13:
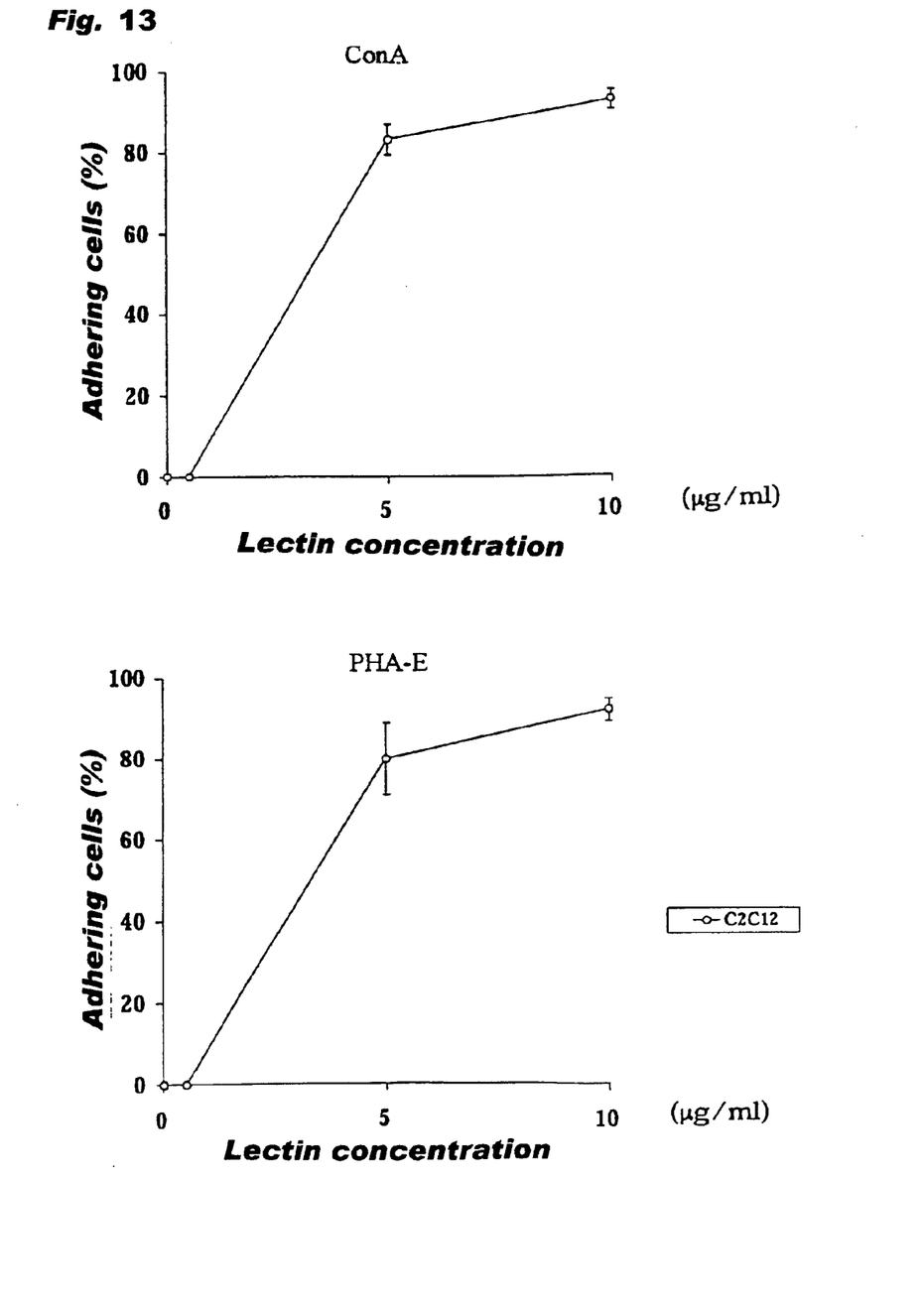
FIG. 13 a graph showing that resistance against proteolytic reaction was conferred to a myoblast cell line by ConA and PHA-E.

In the cells obtained and cultured from tissue (non-cell lines), both ConA and PHA-E inhibited release of cells from the cell layer at concentrations of 5–10 μg/mL (FIG. 10). In the established cell lines including the fibroblast lines (FIG. 11), epithelial cell lines (FIG. 12) and myoblast line (FIG. 13), both ConA and PHA-E inhibited release of cells from the cell layer at concentrations of 5–10 μg/mL. These results indicated that ConA and PHA-E are able to confer resistance against proteolytic reaction to various types of cells and cell lines such as fibroblast cell lines, epithelial cell lines and myoblast cell lines.

INDUSTRIAL APPLICABILITY

The present invention provides resistance-conferring agents comprising lectins as effective components, which are able to confer resistance against external stimulus to animal cells, and particularly mammalian cells (for example, mesenchymal stem cells, osteoblasts, chondrocytes, periodontal cells, dental pulp cells, fibroblasts, epithelial cells and myoblasts), as well as to the cultured cells and various tissues in the living bodies. The agent for conferring resistance to external stimulus of the invention can confer to such animal cells and/or tissues resistance against mechanical stimuli and/or proteolytic reactions, and thereby enhance graft fixation of the cells and/or tissues, as well as transplant tissues obtained by culturing them. The resistance-conferring agents of the invention may therefore be used for treatment of various diseases of the bone, cartilage or teeth which are underway of repair or regeneration and require transplanting of mesenchymal tissue, bone tissue, cartilage tissue, periodontal tissue and dental pulp tissue.

What is claimed is:

1. A method of enhancing the fixation of transplanted animal cells into surrounding tissue, characterized by treating the animal cells with a lectin prior to transplantation, wherein said animal cells are mesenchymal stem cells, osteoblasts, chondrocytes, periodontal cells, dental pulp cells, fibroblasts, epithelial cells or myoblasts, and wherein said transplanted animal cells are fixed in said surrounding tissue.

2. The method according to claim 1, wherein the lectin is used at a concentration of 0.01–1000 μg/mL.

3. The method according to claim 2, wherein the lectin is used at a concentration of from 0.1 to 100 μg/mL.

4. The method according to claim 3, wherein the lectin is used at a concentration of from 1 to 20 μg/mL.

5. The method according to claim 4, wherein the lectin is used at a concentration of from 5 to 10 μg/mL.

6. The method according to claim 1, wherein said animal cells are cultured cells.

7. The method according to claim 1, wherein the lectin is concanavalin A, phytohemagglutinin E, phytohemagglutinin P, or wheat germ agglutinin.

8. The method according to claim 7, wherein the lectin is concanavalin A.

9. The method according to claim 7, wherein the lectin is phytohemagglutinin E.

10. The method according to claim 1, wherein treating the animal cells with a lectin comprises incubating the animal cells with the lectin from 1 minute to 10 days.

11. The method according to claim 10, wherein the animal cells are incubated with the lectin from 1 to 48 hours.

12. The method according to claim 1, wherein the animal cells are from a mammal.

13. The method according to claim 12, wherein the animal cells are from a mouse, rat, rabbit, dog, monkey, cow, goat, sheep, or human.

14. The method according to claim 13, wherein said animal cells are human-derived.

* * * * *